(12) United States Patent
Eckelberry et al.

(10) Patent No.: US 8,993,314 B2
(45) Date of Patent: Mar. 31, 2015

(54) ALGAE GROWTH SYSTEM FOR OIL PRODUCTION

(75) Inventors: Nicholas Eckelberry, Los Angeles, CA (US); T. Riggs Eckelberry, Los Angeles, CA (US)

(73) Assignee: Ennesys SAS, Nanterre (FR)

( * ) Notice: Subject to any disclaimer, the term of this patent is extended or adjusted under 35 U.S.C. 154(b) by 1597 days.

(21) Appl. No.: 11/829,883

(22) Filed: Jul. 28, 2007

(65) Prior Publication Data

US 2009/0029445 A1  Jan. 29, 2009

(51) Int. Cl.
*C12M 1/00* (2006.01)
*C12M 3/00* (2006.01)
*C12M 1/04* (2006.01)

(52) U.S. Cl.
CPC ............ *C12M 31/10* (2013.01); *C12M 21/02* (2013.01); *C12M 27/04* (2013.01); *C12M 29/26* (2013.01)
USPC ................. 435/292.1; 435/257.1; 435/259; 435/293.1; 435/293.2; 435/309.1; 47/1.4

(58) Field of Classification Search
CPC ...... C12M 21/02; C12M 31/10; C12M 31/02; C12M 31/08; C12M 23/06; A01G 33/00; C12N 1/12; C02F 3/32
USPC ............. 435/257.1, 259, 292.1, 293.1, 293.2, 435/309.1; 47/1.4
See application file for complete search history.

(56) References Cited

U.S. PATENT DOCUMENTS

| | | | | |
|---|---|---|---|---|
| 4,981,582 | A * | 1/1991 | Yoon et al. | 209/164 |
| 5,866,910 | A * | 2/1999 | Cooke et al. | 250/438 |
| 2004/0096943 | A1 * | 5/2004 | Marx et al. | 435/69.1 |
| 2006/0141615 | A1 * | 6/2006 | Lu | 435/292.1 |
| 2006/0240544 | A1 * | 10/2006 | Shiau | 435/289.1 |
| 2009/0047722 | A1 * | 2/2009 | Wilkerson et al. | 435/173.7 |
| 2009/0291485 | A1 * | 11/2009 | Shigematsu et al. | 435/257.1 |
| 2010/0005711 | A1 * | 1/2010 | McNeff | 47/1.4 |
| 2010/0034050 | A1 * | 2/2010 | Erb et al. | 366/342 |

OTHER PUBLICATIONS

Merriam-Webster online (merriam-webster.com/dictionary), definition of fluid (printed on Sep. 8, 2010).*
Wilkerson et al. U.S. Appl. No. 11/608,527, filed Dec. 8, 2006.*
Selvaraj et al., "Biodesulfurization of Flue Gases using Synthesis Gas Delivered as Microbubbles," American Chemical Society Spring 1997 Symposium.
Brennen et al., "Numerical Computation of Shock Waves in a Spherical Cloud of Cavitation Bubbles," Journal of Fluids Engineering, 1999, pp. 872-880, vol. 121, No. 4.

* cited by examiner

*Primary Examiner* — Michael Hobbs
(74) *Attorney, Agent, or Firm* — IM IP Law PLLC; C. Andrew IM

(57) ABSTRACT

A system for culturing photosynthesizing microorganisms includes a source of a gaseous fluid a mixer that creates micron bubbles within an aqueous medium using the gaseous fluid. The mixing chamber holds the aqueous medium including the micron bubbles before the micron bubbles and aqueous medium are mixed with a culture of photosynthesizing microorganism in a reaction chamber.

18 Claims, 7 Drawing Sheets

ALGAE GROWTH SYSTEM FOR OIL PRODUCTION

RELATED APPLICATIONS

Not applicable.

FIELD OF THE INVENTION

The invention relates to a method and system for enhancing the colony propagation of micro-algae, diatoms, other microorganisms, especially unicellular organisms and certain prokaryotes specifically including cyanobacteria in a photobio-reactor, e.g., in order to produce oil and bio-fuel stock.

BACKGROUND OF THE INVENTION

The following discussion is provided solely to assist the understanding of the reader, and does not constitute an admission that any of the information discussed or references cited constitute prior art to the present invention.

There has been tremendous interest generated in the production of bio-fuels created from the growing of fast replicating high lipid content prokaryotes and eukaryotes such as diatoms, unicellular organisms and micro-algae for the harvesting of their lipid content. The creation of micro-algae colonies and extraction of triglycerides (TAG) contained therein is of primary interest in the creation of oil and biofuels.

All eukaryotes have a plasma membrane, which is the boundary between the cell and the environment; it is selectively or partially permeable that is: it can accept or reject substances necessary or detrimental to its growth. This membrane is made up of a double sheet of phospholipid molecular material that has the unusual property of being at one end, the head, hydrophilic and the other end, the tail of its beaded shape, hydrophobic. This phospholipid material is of particular interest to the growing and harvesting of TAG's as a substitute for petroleum, as it is both the hydrophilic and hydrophobic qualities of this material that the present invention seeks to exploit.

"In turbulence, phospholipids form two kinds of bubbles: a monolayer that can only capture a drop of oil and a bilayer that can capture a drop of water. The bilayer allows the hydrophobic tails to associate with themselves, while the heads associate with water on both the inside and the outside surfaces of the bubble." It is thought that phospholipids were originally grouped together in eddies and calmer waters of the primordial oceans through the action of micron-bubbles, that is a foam that was made up of millions of bubbles created by the breaking of waves. Around these bubbles, these exotic molecules grouped and, throughout the millennia, grew into structures that give us the basic design of the Eukaryote.

Some small eukaryotic organisms, e.g., unicellular microalgae and diatom colonies, grow naturally very fast provided optimum conditions are present to promote their propagation, a fact witnessed by pool and aquarium owners. The challenge associated with specialized, controlled eukaryote growth of eukaryotic microorganisms such as diatoms and micro-algae for harvesting purposes has been duplication of the natural growth promoting environment, to wit: Thorough exposure to $CO_2$, growth promoting admixtures, exposure to light and in the final stage, extraction, which is a term describing the breakdown of the plasma membrane to extract the encysted fatty acid material known as triglycerides or TAGs.

SUMMARY OF THE INVENTION

The present invention concerns advantageous systems for the growth and processing of microorganisms, e.g., for the extraction of lipids. Such lipids can, for example, be used as a fuel or fuel feedstock, such as for production of biodiesel, as well as other fuel compositions and applications in which a biologically produced hydrocarbon substitute is beneficial. Thus, the invention concerns a biological growth reactor vessel for the cultivation of micro-algae, diatoms or other unicellular organisms which incorporates a dispensing rod to which are attached a plurality of clear paddles which increase surface area for the diffusion of light and growth enhancing admixtures such as $CO_2$, nitrogen and cellulose premixed at micron level. The dispensing rod incorporates a plurality of holes strategically placed to disperse the micron-mixture slurry of the growth admixtures. The dispensing rod and its attached clear paddles make use of methods and technologies to concurrently micron mix admixtures such as natural gases, amendments and other biological factors such as enzymes and microbes to increase contact area between said mixtures and micro-algae, diatoms or other naturally occurring unicellular growth. The dispensing rod can also be used in a strategic moment in time to introduce a high concentrate of micro-bubbles and optionally micron-mixed catalase enzymes and other cellulose break-down admixtures and gases to enhance rupturing of cell walls in order to extract the maximum amount of triglyceride content from both intra and extra-cellular walls of said micro-micro-algae, diatom or other microorganism, especially other eukaryote. While the current invention is particularly advantageous for the growth and breakdown of micro-algae within a single or serially positioned photo bio-reactor, the invention also relates to the use of the dispensing rod in an outdoor pond or any other similar cultivation systems.

Thus, a first aspect of the invention concerns a system for culturing photosynthesizing microorganisms. The system includes a mixer which creates micron bubbles within an aqueous medium, a mixing chamber having fluid connection with the mixer. The medium mixed in said mixer may, when desired, be held in the mixing chamber. The system also includes a reaction chamber having fluid connection with the mixing chamber and including a light distributing and fluid dispensing rod. The photosynthesizing microorganisms are grown in the reaction chamber.

In particular embodiments, the mixer is or includes a static mixer; a static mixer can include a flow constrictor and an entrainment tube immediately upstream thereof, where the entrainment tube delivers a gas or a liquid or both into a fluid stream passing through the mixer (the mixer may also include more than one, e.g., two, entrainment tubes, which may be used separately); the mixer can generate bubbles of less than 100, 80, 70, 60, 50, or 40 micrometer, or even smaller.

In certain embodiments, the light distributing and fluid dispensing rod includes a central tube having at least one fluid path (usually at least one internal fluid path), a plurality of perforations in the fluid path, a plurality of light conducting panels attached around the central tube, and at least one light path that provides for light emission from the light conducting panels. In further embodiments, there are 2, 3, 4, 5, 6, 7, 8, 9, 10, or more light conducting panels, or at least those number of panels, or 2-5, 4-8, 5-10, or 7-15 panels; at least some of the light conducting panels are colored; at least some of the light conducting panels include light sources, e.g., light emitting diodes (LEDs); at least some of the light conducting panels are fixed with respect to the central tube; at least some of the light conducing panels can rotate with respect to the central tube (e.g., passively); at least some of the light conducting panels are mounted on shafts that pass through or are attached to the central tube; at least part of the outer surface of the central tube is mirrored; the central tube is straight; the central tube includes curves, e.g., is wavy or approximately sinusoidal; at least some of the light conducting panels are substantially flat; at least some of the light conducting panels have curved upper and lower surfaces.

Further, in certain embodiments, the reaction chamber includes an inwardly directed mirrored surface (e.g., with the mirroring on the inside or the outside of the reaction chamber wall); the reaction chamber includes at least one light source oriented to emit light into said reaction chamber; a light source includes a plurality of light emitting diodes (LEDs).

In further embodiments, the system also includes a collection tank having fluid connection with the reaction chamber; the system also includes computer controls to regulate culture conditions and/or cell disruption conditions.

In a related aspect, the invention provides a dispensing rod for a microorganism culture system, e.g., a dispensing rod as described for the preceding aspect. Thus, the dispensing rod includes a central tube that has at least one fluid path with a plurality of perforations in the fluid path, and a plurality of light conducting panels attached around the central tube, where the tube and the light conducting panels together include at least one light path that provides for light emission from the light conducting panels.

In particular embodiments, the dispensing rod is as described for the preceding aspect; the dispensing rod is sized and configured to fit in a pre-selected reaction chamber of a microorganism culture system.

Another related aspect concerns a method for culturing photosynthesizing microorganisms, where the method includes growing the microorganisms in a culture system that includes a mixer which creates micron bubbles within an aqueous medium, a mixing chamber having fluid connection with the mixer. Usually, the medium mixed in the mixer is or can be held in the mixing chamber (e.g., to allow bubble reconfiguration to a more stable bubble size distribution from a less stable distribution), and a reaction chamber having fluid connection with the mixing chamber and including a light distributing and fluid dispensing rod, where the photosynthesizing microorganisms are grown in the reaction chamber. Preferably, nutrients and light are introduced into culture medium in the reaction chamber through the dispensing rod.

In particular embodiments, the culture system is as described for the first aspect above or otherwise described herein for this invention.

In certain embodiments, the method also includes cleaning the reaction chamber (and optionally the mixing chamber) between microorganism growth batches using a micron mix of cleaning agents or sterilization agents or both, e.g., agents passed through the mixer of the system; the cleaning agents or sterilization agents include ozone; the reaction chamber is exposed to ultraviolet light between microorganism growth batches.

Yet another related aspect concerns a method for producing lipids, which includes growing photosynthesizing microorganisms in a culture system, where the system includes a mixer which creates micron bubbles within an aqueous medium, a mixing chamber having fluid connection with the mixer, and a reaction chamber having fluid connection with the mixing chamber and including a light distributing and fluid dispensing rod. The photosynthesizing microorganisms are grown in the reaction chamber. Preferably, wherein medium mixed in said mixer is or can be held in the mixing chamber. Also preferably, nutrients and light are introduced into culture medium in the reaction chamber through the dispensing rod. The method also includes extracting lipids from the microorganisms following growth.

In certain embodiments, the medium is held in the mixing tank for a period sufficient for the bubbles to reconfigure to a configuration such that bubble collapse upon introduction of the medium into the reaction chamber does not significantly rupture cells; the medium is held in the mixing tank for a period of 3, 4, 5, 6, 7, 8, 9, or 10 minutes, or for 3-10, 3-7, 4-7, or 4-6 minutes.

Preferably the method also includes rupturing cells of said microorganisms following growth; the rupturing involves exposing the cells to collapse of bubbles having an average diameter of less than 100, 90, 80, 70, 60, 50, or 40 micrometer or even smaller; the rupturing further includes exposing cells of the microorganisms to one or more enzymes (e.g., catalase) that weaken cell walls before or during the collapse of the bubbles; the method also includes cleaning the reaction chamber between growth batches of the microorganisms.

In particular embodiments, the microorganisms are microalgae or diatoms.

In certain embodiments, the culture system is as described for the first aspect above; the method of growing the microorganisms is as described for the preceding aspect.

As used herein, the term "photosynthesizing microorganism" refers to a microorganism that is capable of utilizing light as an energy source and fixing carbon from carbon dioxide in organic compounds.

The term "system for culturing photosynthesizing microorganisms" refers to a man-made culture system that includes a chamber or other container for holding culture medium and also includes the capability to deliver light of appropriate intensity for growth of a selected microorganism to culture medium in the chamber or other container. In many cases the system will also include reservoirs, pipes, pumps, and the like for supplying nutrients, water, and other chemicals, and for removing culture solution containing the microorganisms.

In connection with the present invention, the term "micron bubbles" refers to air bubbles within an aqueous medium such that the median bubble size (referred to herein as average bubble size or diameter) is no greater than 100 micrometer (microns). In most cases, the average bubble size will be no greater than 60 micrometer.

In connection with the present systems, the term "mixing chamber" means a tank or other container or reservoir which receives liquid from a mixer and holds the liquid until release or transfer to another part of the system is desired. The mixing chamber will usually include a fluid connection with the mixer such that liquid can be cycled multiple times through the mixer and mixing chamber.

Likewise in connection with the present systems, the term "reaction chamber" means a tank, tub or other container or reservoir (even including a pond or pool unless indicated to the contrary) in which significant growth and/or cell disruption occurs during operation of the system. Usually the reaction chamber is configured to accept liquid from a mixing chamber. A reaction chamber may also have a fluid connection with a collection chamber.

Similarly, as used in connection with the present systems, the term "collection chamber" refers to a tank or other reservoir that is connected to other components of the system such that material from the reaction chamber may be held as desired, e.g., concentrated or un-concentrated biomass from the growth of microorganisms.

In the context of the present invention, the term "light distributing and fluid dispensing rod", or simply "dispensing rod" refers to a system component which has an elongated generally central component generally in the shape of a shaft or tube. The rod includes at least one light path and/or light sources such that light can be emitted from the light distributing and fluid dispensing rod. In most cases, the rod includes paddles mounted on and extending from the central rod. The rod also includes at least one fluid path that has perforations or other apertures that allow fluid in the fluid path to leave the fluid dispensing rod at multiple locations. For example, the dispensing rod may be a tube, i.e., having a hollow interior, with perforations in the wall of the tube. Other arrangements are also possible.

As used in the context of a fluid dispensing rod, the term "perforations" refers to openings or short passageways in the wall of a container or passageway allowing fluid passage through the perforation. For a fluid path in or on a dispensing rod, perforations in the wall of the passageway defining the fluid path are present to allow fluid to exit from the fluid path into the reaction chamber.

The phrase "light conducting panels" refers to substantially sheet-like or plate-like structures that are sufficiently transparent that light can pass through them and/or that contain light conducting components such as optical fibers. Transparent light conducting panels may be colored, but not to a degree that prevents useful intensities of light from being transmitted through the panel into the panel's surrounding environment. In many cases, such panels will be "substantially flat", meaning that the panels are substantially planar, e.g., deviating no more than 15 degrees, and preferably no more than 10 or 5 degrees from a line normal to the long axis of the paddle and parallel to the surface from one lateral edge of the paddle.

In the context of the present light distributing and fluid dispensing rod, the term "light path" refers to a part of the dispensing rod through which a large proportion of incident visible wavelength light can pass. Examples include air spaces and transparent solid materials, e.g., transparent glass or plastic paddles, optical fibers, and the like. Within the present dispensing rods, such a light path provides for "light emission" from the paddles; that is, light conducted through the paddles through one or more light paths exits the paddles and enters the surrounding environment (e.g., into growth medium surrounding the paddles).

Indication that paddles "attached around the central tube" or "attached around the central shaft" of a dispensing rod means that the paddles are attached to the tube or shaft with sufficient strength that the paddles extend substantially outwardly from the axis of the tube or shaft. Usually the included angle between the axis of the tube or shaft and a line on the surface of the paddle extending radially from the central tube or shaft is approximately 90degrees (i.e., approximately perpendicular), but may be less, e.g., at least 60, 70, or 80 degrees. In most cases, the attachment between the paddle and the central tube or shaft is essentially rigid, e.g., on a stiff shaft or mounting stud. However, in some case, there is flexibility in the mounting, e.g., allowing up to about 3, 5, or 10 degrees of flexing under forces encountered during normal operation of reaction chamber containing the dispensing rod.

In the context of the present reaction chambers, the term "mirrored surface" refers to a visible light reflective surface, usually a coated surface where the coating significantly increases the reflectivity and/or longevity of the reflectivity. Such coatings include, for example, silver and aluminum coatings. Such a mirrored surface reflects at least 80% of the incident light in the range of 550-600 nm when clean, and preferably at least 85, 90, or 95%.

As used herein, the term "light source" means a visible light generating device, e.g., a light emitting diode.

In the context of the present dispensing rods, the term "central tube" refers to a hollow structure, i.e., a tube, that is located with paddles distributed around it such that with the extreme distal ends of the paddles defining a cylindrical surface, the tube is approximately at the central axis of the cylinder.

Also in the context of the present dispensing rods, the term "fluid path" means a passageway through which a fluid, generally a liquid, flows. For the present dispensing rods, the fluid path in or on a dispensing rod allows a liquid to pass through the fluid path and pass into the reaction chamber. Further, the term "internal fluid path" refers to a fluid path internal to the dispensing rod, e.g., through the hollow interior of a dispensing rod that is a tube.

As used herein, the term "mixer" refers to a device that will vigorously mix a liquid, and will preferably create a large number of bubbles when air or other gas is introduced into the mixer. In this context, the term "static mixer" refers to a mixer than does not include internal moving mechanical parts. Generally this means that the fluid is mixed as it passes through the mixer. For this invention, such a static mixer also allows introduction of liquids and/or gases and mixes them with the bulk fluid.

In reference to a mixer, the term "flow constrictor" means an internal component in a mixer that substantially reduces the cross-sectional area of the fluid flow passageway, e.g., a venturi. In a static mixer, such a flow constrictor is normally followed by a region of expanded cross-sectional area, e.g., to approximately the same cross-sectional area as that preceding the flow constrictor.

Also in the context of a mixer, the term "entrainment tube" refers to a tube or aperture leading from outside the mixer to inside the mixer through which additional materials, typically liquid and/or gases can be directed into the fluid passing through the mixer. In a static mixer having a flow constrictor, such entrainment tube is usually immediately upstream of or within the flow constrictor. There may also be more than one entrainment tube, allowing introduction (i.e., entrainment) of more than one material separately.

Unless clearly indicated to the contrary, as used herein the term "medium" refers to an aqueous, liquid solution or suspension. In most cases, the term medium refers to a growth medium.

In the context of the present systems, the term "cleaning agent" refers to a material that removes a substantial portion of organic accumulation (e.g., biological deposits). Such cleaning agents may include, or example, surfactants, enzymes, and the like. Similarly, the term "sterilization agent" refers to a chemical agent (e.g., ozone and alcohol), and/or electromagnetic radiation (e.g., UV light) that kills residual cells, e.g., residual bacterial and/or algal cells. It can be advantageous to use such cleaning agents and/or sterilization agents in the present systems, e.g., for the reaction chamber including the dispensing rod.

In the present context, the terms "rupturing cells", "cell rupture", and the like refer to cell lysis, that is, at least creating a hole in the cell wall (if present), and cell membranes of cells, allowing the internal contents of the cells to substantially leak out of the cells. For example, such cell rupture may be accomplished by physical forces and/or chemical treatment and/or enzymatic treatment.

Additional embodiments will be apparent from the Detailed Description and from the claims.

DETAILED DESCRIPTION OF THE PREFERRED EMBODIMENTS

Figure 1:
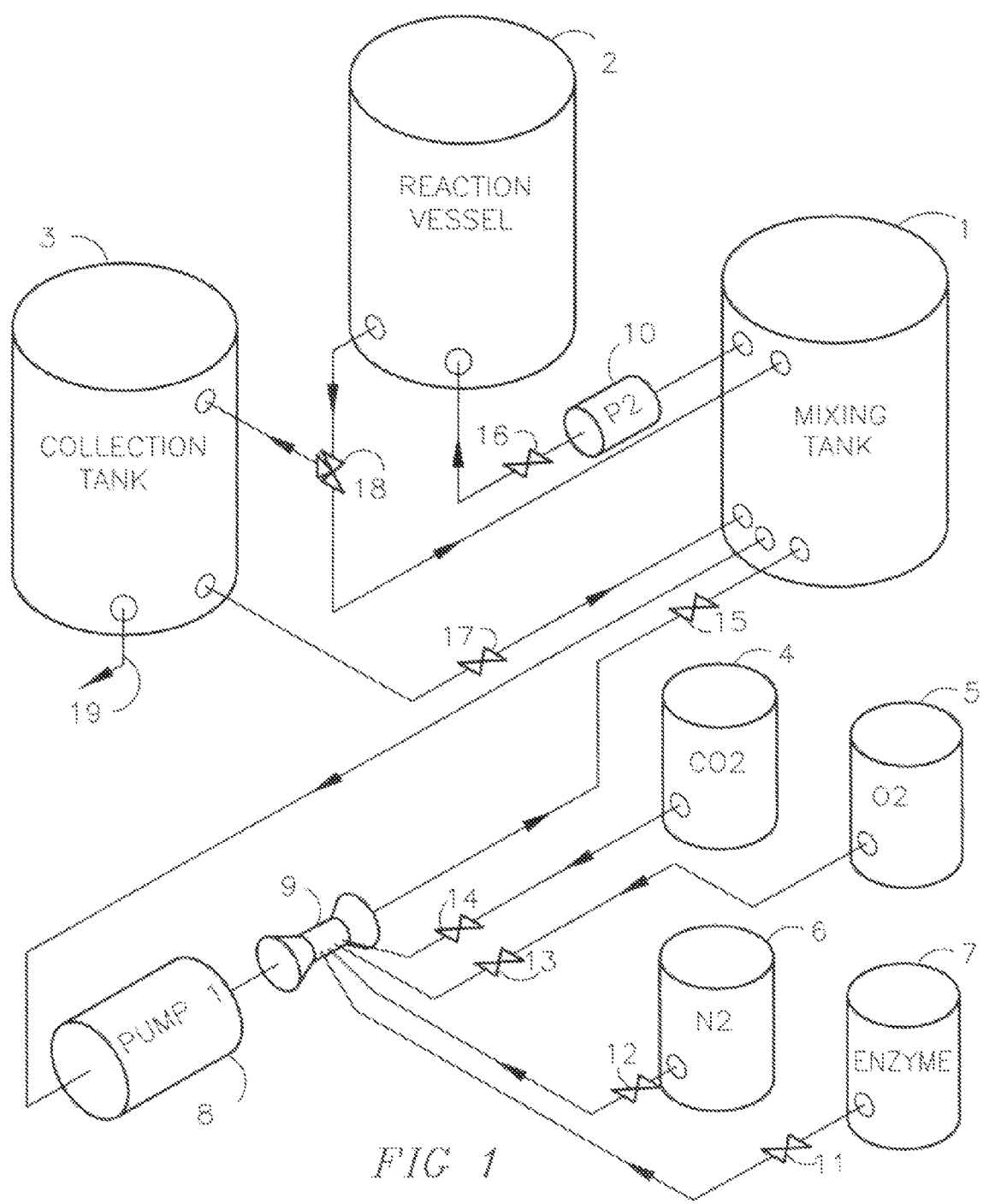
FIG. 1 shows a schematic of an exemplary system for the present invention, including mixer, mixing tank, reaction vessel (reaction chamber or growth tank), and collection tank.

The present invention concerns methods and systems for enhancing growth of photosynthesizing microorganisms such as algae, diatoms, and the like, and/or for accelerating or otherwise enhancing disruption of such microorganism cells. Still further, the invention concerns a method and apparatus for cleaning the growth and/or cell disruption system. Thus, the invention concerns the methods, the combined systems, and the component sub-systems.

Though the present systems and methods can be implemented in a variety of ways, in general the method and systems utilize fluid manipulation, e.g., through shear, flow turbulence, laminar films and more specifically bubble size from fine through micron to nano sized bubbles in correct sequences in the growth and/or extraction processes. Thus, it was found that differing conditions in fluids can optimize both growth and decay of micro-algae and other such microorganisms, thereby providing advantageous processes and systems for utilizing microorganisms, especially for lipid production and extraction.

In certain beneficial embodiments, the invention utilizes an integrated system that is configured to be used in batch mode for both growth and cell disruption, and that can be readily prepared for subsequent batches. As discussed in greater detail below, in general terms, the system includes a static mixer, a mixing chamber, and a bio-reactor. Of course, a complete system will also usually include associated components, e.g., associated controls, tubing, storage containers, and the like.

As indicated, the exemplary system includes a static mixer (with associated pump(s), tubing, controls, etc.) that is used to create extremely fine bubbles and distributed nutrients. This mixer is associated with a mixing chamber or tank, such that medium is pumped through the static mixer and into the mixing chamber.

Thus, the present invention concerns systems and methods that utilize micron mixing to create finely distributed nutrients for the growth phase, without subjecting the organisms to shock waves that disrupt the cells. The shock waves are avoided by allowing microbubbles to collapse before introducing the mixed medium into the growth environment. The growth is preferably carried out in an environment that includes a light distributing dispensing rod. The precise culture conditions can be controlled to maximize growth and/or production of a desired cell component, e.g., lipids. Following growth, the cells can by disrupted using shock waves produced by collapse of micron bubbles generated by the same or another mixer as was used to produce the finely divided nutrient mixture for the growth phase. The cell disruption can be carried out in the same or different chamber as was used for growth. Following cell disruption, the desired component (e.g., lipid) is extracted, e.g., using conventional extraction methods. Most often, such extraction is carried out using different apparatus than was used for the growth and cell disruption. It can also be advantageous to clean and/or sterilize the growth (and/or cell disruption) chambers prior to re-use. Such cleaning and/or sterilization can utilize finely mixed chemicals, e.g., ozone, and also can use sterilizers such as UV light.

Thus, the entire process can be considered as including multiple component processes, e.g., including growth, cell disruption, extraction, and system cleaning. Those sub-processes are described below along with exemplary associated systems.

A. Growth Enhancement

1. Nutrient Availability

Conceptually, the first part of this invention involves the growth of the microorganisms. In particular, such growth involves the use of micron-mixing to create extremely fine blends of gas and amendments, to promote the growth of micro-algae or other microorganisms. A suitable blend of nutrients for the particular microorganism is processed to generate an extremely fine emulsion or slurry, generally in an aqueous medium.

For example, nutrients, such as $CO_2$, and nitrogen (e.g., as nitrates), vital for the optimized growth of micro-algae can be injected at micron-level through entrainment through a venturi positioned within a static mixer. The product (typically a fine emulsion or slurry) is then introduced to the reaction vessel. This process causes the interfacial area (mass transfer) to be increased and therefore the contact zone between micro-algae and amendments is promoted. The increased nutrient transport can enhance the growth of the microorganisms.

In an illustrative study, the authors focused on utilizing a gas mixture containing 36% $H_2$, 47% CO, 10% $CO_2$, 5% $CH_4$ and a balance of $N_2$ as a model coal synthesis gas as a low-cost feedstock for sulfate-reducing bacteria (SRB) cultures. Coal synthesis gas is readily available in power plants and the biological utilization of syn-gas as a carbon and energy source produces no organic end product that has to be processed prior to its disposal. Coal synthesis gas is, however, sparingly soluble in aqueous phase. This process utilizing SRB with syn-gas feedstock may be mass transfer limited and methods to enhance the mass transfer have been investigated. A continuously stirred tank reactor (CSTR) with cell recycle and a trickle bed reactor with cells immobilized in BIO-SEPTM polymeric beads were operated with syn-gas feedstock to obtain maximum productivity for $SO_2$ reduction to $H_2S$. The CSTR reactor was then fed with syn-gas as microbubbles in an effort to improve the mass transfer properties. With syn-gas fed as microbubbles, productivity in the CSTR increased from 1.2 to 2.1 mmol/h L in 33 h. This has been observed at the same biomass concentration of 5 g/L. This shows the mass transfer limitation in the above process. In the trickle bed reactor, maximum productivity of 8.8 mmol/h L was achieved with less carbon and energy requirements (1 mol $H_2$ and 1.2 mol CO per mol of $SO_2$) indicating better surface to volume ratio with cells immobilized in the pores of polymeric beads. SELVARAJ et al., "Biodesulfurization of Flue Gases using Synthesis Gas Delivered as Microbubbles, "American Chemical Society Spring 1997 Symposium.

Though entrainment of nutrients is effective to for improving mass transfer in culture systems and the growth rates of the microorganisms being grown, it is also highly beneficial to avoid the effect of shock wave propagation and attendant ultra-sonic effect that occurs upon collapse of the bubbles. (These effects are described below in connection with degradation of cells and extraction of lipids.) For example, in a slurry or emulsion containing large numbers of micron and/or nano-sized bubbles, the micron slurry is allowed to reconfigure in the mixing tank prior to dispersal in the growth or reaction tank. This reconfiguration allows many of the bubbles to collapse so that a shock wave is not created in the growth chamber.

In our studies, we have found that the process of reconfiguration; that is return to fine bubble state from the micron/nano bubble state, occurs in approximately five minutes. At the end of this period of time, the bubbles have regained roughly their normal size, but the interfacial mass transfer aspect of the mixing is imbedded as a fine colloidal suspension of amendments or admixtures throughout the mix. It is therefore at this point that we introduce the slurry to the reactor vessel and achieve mass transfer or total contact of amendments at a fine bubble level.

In a further development, the use of micron mixing of a growth compatible surfactant, such as suitable oils (e.g., algal oil) can be used to impart a phospholipid quality or sheen to the slurry. Micron mixing in the tank of amendments with the addition of an oil surfactant can result in one or both of two recognized benefits (others may also occur): 1. the concurrent micron mixing of oil and water creates a colloidal mix of oil and amendments which will act, as in nature, as buoys or safe havens for the promotion of new colonies. 2. When oil is micron-mixed, we have observed that the wave collapse or cavitation effect of oil and water at micron level generates a tremendous amount of heat. This heat enhances growth in the reaction vessel.

Of course, the particular conditions for growing a desired microorganism can be adjusted and/or optimized for that organism. A person skilled in the field can readily determine advantageous growth conditions, e.g., that provide a beneficial combination of growth rate, relative levels of production of a desired product (e.g., lipids), and ability to rupture cell walls.

A variety of different microorganisms can be used for lipid production, including, for example, algae, diatoms, and cyanobacteria. Non-limiting examples include the following organisms: Neochloris oleoabundans—a microalga belonging in the class Chlorophyceae; Scenedesmus dimorphus—a unicellular algae in the class Chlorophyceae; Euglena gracilis; Phaeodactylum tricornutum—a diatom; Pleurochrysis carterae—a unicellular coccolithophorid alga of the class Haptophyta (Prymnesiophyceae; Prymnesium parvum; Tetraselmis chui—a marine unicellular alga; Tetraselmis suecica; Isochrysis galbana—a microalga; *Nannochloropsis salina* or other *Nannochloropsis* sp.; *Botryococcus braunii* or other *Botryococcus* sp.—a green alga; *Dunaliella tertiolecta; Spirulina* species; strains of *Chlorophyceae* (green algae); *Bacilliarophy* (diatom algae).

2. Light Control and Exposure

Another major problem in accelerating growth cycles has been the proper distribution of light to the culture. Light is a key component, along with CO2 , for rapid bio-mass or colony creation of photosynthesizing microorganisms within a reaction vessel. Light is so critical to growth that the industry has created reactor shapes and materials to increase diffusion of light into the growth medium.

Thus, the systems of this invention can advantageously include light distribution channels that provide penetration of light at appropriate levels for growth deep into the culture.

One example of enhancing light into a culture is described in Trosh, U.S. Pat. No. 6,509,188 which increases light distribution surface area through the use of a plurality of panels placed on the inside of a growth tank or bio-reactor. This embodiment, while laboratory proven to increase light within the reactor, would prove hard to mass manufacture and maintain as the stresses such as water weight and flow placed upon these panels would cause deterioration and failure unless they were made of one mold, which substantially increases cost and impracticality for use in industrial settings.

An advantageous design that overcomes limitations of the Trosh approach is described below. This design, in fact, provides a multi-function design.

3. Paddle System for Combined Nutrient Injection and Light Distribution and Bio-Reactor Tanks In this invention, light conductors and/or sources are commonly used that delivery light deep into the culture. Highly preferably, the intensity of the light and/or the wavelength of the light are controlled to reduce or prevent damage to the organisms (e.g., bleaching).

An advantageous embodiment utilizes a dispensing rod that has a paddle system. The paddle system increases light interfacial area. The paddle system also enhances vortex creation, thereby creating low pressure eddy zones that promote colony aggregation. The paddles' positions and shapes also have the benefit of distributing micron-mixed CO2 and nutrients for the growth cycle along certain laminar flows, causing further disruptions and disturbance in order promote contact of nutrients with the permeable plasma membrane of the micro-algae.

In many cases, the dispensing rod is a tube that can be scalable to essentially any size installation indoor or out. Furthermore such dispensing rods can be retrofit to most installations. The dispensing rod is generally inserted in either a reaction vessel (of essentially any size or shape) or a pond. Usually the dispensing rod is inserted in the middle or approximate middle of the vessel or pond. The dispensing rod is usually a hollow tube (which may be mirror plated) that has paddles distributed along and extending outward from the rod. The paddles may be attached in a manner allowing them to change angle, e.g., on bearings or a centrally positioned axle that runs through the tube. In other cases, the paddles are mounted with fixed angle. Similarly, the entire dispensing rod can be mounted such that it can gently sway and/or gently rotate, or it can be fixed. Furthermore, the central tube or shaft of the dispensing rod can itself be flexible, such that flow within the medium in the reaction chamber can cause that tube or shaft to flex.

The paddles may be constructed in a variety of different shapes and/or materials. In many cases, the paddles are clear plastic or glass or similar transparent material. The paddles transmit light (preferably diffuse) and enhance the motion of the overall fluid. The paddles may be colored, if desired, to reduce or block light of certain wavelength from being transmitted into the culture. As indicated above, these paddles increase the surface area for both light and reaction. They are commonly not motor driven, but rather flow driven. Their purpose is especially to increase the surface area for light transmission and to create low pressure zones where microalgae growth can be enhanced.

Especially when used in a tank-type bio-reactor, the paddles can be constructed to reach almost to the edge of the outer vessel to maximize flow dispersal and light diffusion, while still providing enough space to permit motion throughout the reactor ensuring stagnation pockets do not coalesce.

Because the flow interferences (paddles) are on the exterior of the central rod or tube, the system is relatively inexpensive to manufacture and implement and maintain. Furthermore the embodiment can be used in both bio-reactors and pond use with minor modification; furthermore the growth stage and extraction stage are within the same reactor vessel, saving both time and money.

Also as indicated above, these paddles increase the surface for both light and reaction area. They are commonly not motor driven, but rather flow driven. Their purpose is especially to increase the surface area for light transmission and to create low pressure zones where micro-algae growth might be enhanced.

The light can be generated and/or introduced in a variety of ways. Thus, the light source can emanate from either end of the reaction vessel and/or the sides. In an outdoor pond, at least a significant portion of the light will emanate from the sun. The light can be transmitted and/or reflected both on/through the paddles and mirrored surface of the central tube; a convex mirror at either end can be attached to increase light refraction. The light can be regulated as to color (i.e., wave length) intensity, and/or time, e.g., using manual regulation and/or computer control. Thus, light can be introduced from the top and or bottom and/or paddles.

To enhance the distribution of light, the bio-reactor can have a mirrored surface (e.g., on the outside of the growth tank) pointing inwards that reflects as much light as possible into the growth medium in the tank. Similarly, the dispensing rod may be mirrored. The benefit of such mirroring is to increase the opportunity for exposure of the microorganisms to appropriate light and reducing loss through or into surfaces of the bioreactor.

The mirrors can be made of any of a variety of reflective materials, e.g., from standard silver coating to esoteric materials such as silicates. Also, a number of different light sources and/or conductor can be used alone or in combination, e.g., fiber optics and/or light emitting diodes (LEDs). For example, fiber optics can be run to desired light introduction locations, e.g. through the paddles), and/or LED lights can be placed at strategic points (e.g., in or on the paddles and/or on the walls of a tank-type reaction chamber, among others).

In addition to the light distribution and flow modification functions, the rod is also used to introduce fluids. The rod has a plurality of holes that disperse the mix of micron-bubbles, e.g., created by a static mixer, dynamic mixer or other device that mixes both elements and water at micron level and pumps $CO_2$ and nutrients (slurry) in proper ratios.

The combining of both the paddles, distribution holes within the tube and the use of micron-mixing using reactors such as the one found in Uematsu et al 6,279,611 provide elements that will allow those skilled in the art to replicate better conditions in order to promote growth of microorganisms, e.g., colony growth of micro-algae.

In the present exemplary embodiment, the whole of the reaction from growth to extraction occurs in one reaction chamber, one mixing tank, and an extraction vessel. This process system innovation is possible because of methods using micron bubble/mass transfer and fluid disturbance technology in the complete cycle of growth, extraction and disinfection.

In addition, while the present system is primarily described in terms of a single batch system, in-line reaction chambers for serial applications can also be used, with staged growth and extraction cycles. Furthermore, continuous-flow systems can also be constructed in which a portion of the microorganisms from the growth chamber are removed (e.g., by centrifugation) and transferred to a bio-reactor for cell disruption.

B. Cell Disruption

Once the desired microorganisms are grown to a suitable level, the microorganisms (e.g., micro-algae) are removed from the culture conditions (e.g., either with the growth bio-reactor or in a separate bio-reactor). This invention provides beneficial developments on the principle that micron mixing and the production of micro-bubbles further enhances cellulose membrane breakdown admixtures, enzymes, as well as gases such as ozone and other chemicals in order to take advantage of the mass transfer aspects of both amendments and matrix being in a micron state at the same moment in time. Furthermore, since most micro-algae extraction methods have concentrated on preserving cartenoids (also referred to as carotenoids) for their protein and carbohydrate content, they have not used the very powerful shear, ultrasonic generation and oxidizing effects of micro-bubbles. Since it is the principal use of this invention to extract only the lipid content of the micro-algae, we are not restricted by such constraints.

In the current art, e.g., as described in Kanel U.S. Pat. No. 5,951,875, flocculants, chemical means and coagulants are used to separate the micro-algae from brine in order to refine Cartenoids from micro-algae. In that approach, a close contact between fine bubbles and cells is promoted by frothing and the use of fine-bubbles generated by a static mixer/venturi. However, that approach has not discussed the use of micron and sub micron-bubbles defined as under 60 mp throughout the extraction cycle.

Also, recently it was found that the use of ultra-sound in a growth reactor promotes micro-algae cell collapse. In the state of the art (e.g., as described in U.S. Pat. No. 6,540,922 Cordemans et al.), an ultra-sound generator is used in a micro-bubble field to enhance cellular breakdown.

In contrast, we have found that by using certain static mixers, including but not limited to the particular mixer described in U.S. Pat. No. 6,279,611 Uematsu (incorporated herein by reference in its entirety), we can generate the same frequencies required to affect cellular breakdown without the added costs of the sound generator.

This is accomplished by generating bubbles with an average size of about 60 mµ or less and causing the bubble field to include both micron and nano bubbles in varying percentages. For example, this can be accomplished using a static mixer that generates appropriately small bubbles and typically using multiple passes with the recirculating pump to decrease the average bubble size. Due to the configuration of the mixing vessel in relation to the reactor vessel, we can introduce this mix of both micron and nano sized bubbles without affecting the content of the reactor. However, by having two vessels, one for mixing and other a reaction vessel, the latter can now act as the implosion vessel. The micron mix of water, air and chemicals will seek to reconfigure in the reaction vessel, e.g., to return to its homeostatic state as found in nature. The characteristic of such extensive mixing of air and water concurrent with other elements as required such as alcohols, ozone and other amendments is fourfold:

1. A micron mix of fluids, air and chemicals, stretched and distended by the repeated passes in a recirculating pump to a hyper-excited state which, upon disgorgement in the secondary vessel creates a shock wave on cavitation implosion within the reaction vessel. A report of such shock wave generation stated that, "It was found that, with strong bubble interaction effects, the collapse of the cloud is accompanied by the formation of an inward propagating bubbly shock wave. A large pressure pulse is produced when this shock passes the bubbles and causes them to collapse. The focusing of the shock at the center of the cloud produces a very large pressure pulse which radiates a substantial impulse to the far field and provides an explanation for the severe noise and damage potential in cloud cavitation". BRENNEN et al., "Numerical Computation of Shock Waves in a Spherical Cloud of Cavitation Bubbles," Journal of Fluids Engineering, 1999, vol. 121, no. 4, pages 872-880,872.

2. The ultrasonic effect created concurrently with the propagation of the shock wave. The value of the shock wave in cell disruption occurs when the stretched bubble is imploded; this can advantageously be accomplished when there are two vessels; a bubble creation/mixing vessel and an implosion vessel. In the present systems this will usually be the bio-reactor, but can be accomplished in a separate implosion vessel.

3. The creation of excessive heat which further oxidizes the micro-algae. This heat is generated by the friction caused by the breakdown of material and the inherent quality of the micron bubble shock wave to propagate and refract on cellulose material.

4. The oxidizing quality of ozone gas mixed at micron level now reconfigured to oxygen, as it has donated it's free radical to the organic material.

Thus, for carrying out extraction, the holding period of the micron mixed fluid in the mixing chamber (used during the growth phase) is dispensed with, and the micron mixture of water and any constituents to be used to assist cell disruption and/or extraction (e.g., enzymes, though the disruption can be performed without enzymes) is flowed directly to the inner dispensing rod and into the reaction chamber, where the cavitation effect promotes the ultra-sonic breakdown of the cell wall and enhanced contact with enzymes (e.g., catalase) and/or other cell disruption or extraction components. The mix of enzyme and bio-mass is then evacuated to a collection tank (e.g., through an out tube) where the mixture now flocculates due to the micro-bubble activity. The bio-mass is removed from the collection tank where it is subjected to further refinements. The water and oil mixture is also removed for processing, e.g., using conventional methods.

While this invention does not focus on new methods of processing of the biomass for use in bio-fuels, as these have been fairly well documented in the art, it is the intent of this invention to provide for processing a bio-mass whose organelle structure is distressed and whose maximum intra- and extracellular lipid content is released into both the biomass and fluid to increase TAG content, e.g., for use in processing, such as transesterification or hydro-cracking, fluid catalytic cracking or other refining processes.

The extraction of lipids can be carried out in various ways. For example, hexane solvent extraction can be used in isolation or it can be used along with the oil press/expeller method to obtain the lipids. For example, after the oil has been extracted using an expeller, the remaining pulp can be mixed with cyclo-hexane to extract the remaining oil content. The oil dissolves in the cyclohexane, and the pulp is filtered out from the solution. The oil and cyclohexane can be separated by means of distillation. These two stages (cold press & hexane solvent) together will be able to extract more than 95% of the total oil present in the algae. Another extraction method is the super critical fluid method (usually using $CO_2$).

It is also further contemplated that the use of a secondary micron-mixer system for the intimate contact between hexane, for example, and the oil water mixture could be incorporated to lower usage of the hexane, as well as other solvents used in the transterification process. This system would usually be added as a peripheral and not included in the collection tank as contamination with a hydrocarbon byproduct could prove hard to eliminate between growth and harvest cycles.

It is also further contemplated that the processing of spent water before discharge into a public sewer system could be handled by an independent system that makes use of the micron mixing of ozone, along with particulate recovery, e.g., through a simple flocculating column attached to the system in order to comply with municipal discharge laws. In regards to air-quality standards, the issue essentially is non-existent in the growth and extraction cycle as the by-product of growing algae is pure oxygen.

Thus, the dispensing rod can also be used to inject micron-sized enzymes and micron-sized breakdown chemicals as needed for the extraction cycle.

C. System Cleaning

An advantageous additional step in the process involves the cleaning and disinfection of the reactor. For this process, the dispensing rod can also be used to inject ozone gas and other disinfectants (e.g., alcohol) for cleaning and/or sterilization between batch growths. For this, a stream of ozone gas and pure cleaning alcohol is entrained through the venturi of the static mixer to add sterilizing factors. The micron mixture of ozone and alcohol is then gushed into the reactor and recycled a few times, and is then dumped into the product tank where solid matter is recovered through an incorporated sieve. Further sterilization effect can be accomplished by introduction of UV light, usually through the same or similar light paths as used for light during growth, e.g., through the paddles.

Spent water after careful pH, DO and BOD/COD content analysis is preferably cycled back to the main mixing tank for re-use, This water would be entrained into the recirculating or mixing tank by the pump therefore achieving an economy of water. One would add water (top off) to the tank on as needed basis and start the cycle all over again with a new incubated batch of micro-algae.

D. Exemplary System

1. Dispensing Rod

Turning to the drawings to clarify the present system, FIG. 1 shows a schematic of a simple exemplary system. The system includes mixing tank 1, reaction vessel (reaction chamber) 2, collection tank 3, carbon dioxide tank 4, oxygen tank 5, nitrogen reservoir 6, and enzyme reservoir 7. Carbon dioxide tank 4, oxygen tank 5, nitrogen reservoir 6, and enzyme reservoir 7 have fluid connections (referring to both gas and liquids) to a mixer 9, controlled by valves 1 1, 12, 13, and 14. Liquid (e.g., growth or cell disruption medium) is passed through the mixer using pump 8. After passing through the mixer, the liquid passes into mixing tank 1 controlled by valve 15. A return pipe allows multiple passes of the liquid medium through the pump and mixer. Medium from the mixing tank is directed into the reaction vessel 2 forced by pump 10 under control of valve 16. Medium from the reaction vessel can be cycled back through the mixing tank through a return pipe controlled by valve 18 (which can alternately direct the fluid to collection tank 3. For cleaning, fluid from collection tank 3 can also be cycled back to mixing tank 1 controlled by valve 17. Following processing, material from collection tank 3 can be removed through outlet 19.

Typically a batch process using such a system with microalgae would take 12-48 hours depending on the genus of micro-micro-algae. One could also build large or small (in parallel) reactor vessels to obtain a desired quantity of end product.

Thus, the reaction vessel generally has input and output valves to moderate the amount of liquid, to control recirculation of liquid, clear accumulated froth, and to empty the reactor. The reactor also preferably has a safety valve to release excess oxygen created during the cycle to prevent excessive pressure build up, though most of the oxygen would be captured during the cycling times.

Liquid flowing into the reactor from the mixing tank generally flows through a dispensing rod (e.g., as described below) in the reactor. The outflow pipe from the reactor handles the overflow or circulation aspect, it is connected to the mixing tank with a split off valve (18) that disgorges into a product collection tank (3) (broken micro-algae and biomass). From the collection tank, outflow pipe 19 allows spent water to be drained from product (e.g., to the sewer or recycled into the beginning of the system).

Highly preferably there is a separator, e.g., a membrane or filtration sieve that prevents micro-algae from slipping into the stream from the reactor and/or the collection tank and cycling back through the mixing vessel.

As indicated above, the reactor 2 is connected to a recirculating mixing tank 1 and a mixer (e.g., a static mixer) 9. The CO2 and other nutrients are entrained in the medium (e.g., through a static mixer) such that they are micron-mixed and the medium passes into the mixing tank. The mass transferred mixture or slurry is allowed to reconstitute to fine bubble (e.g., 5 minutes or less). A valve 16 is then opened and the micron mixture of CO2 and nutrients (slurry) is then propelled through the dispensing rod to the reactor 2 by the force of burst activated recirculating positive displacement pump until the bio-reactor has a fresh load of CO2 and incubated micro-algae. In the case of a parallel reaction tank application, negative displacement pumps can be added to enhance the propelling of slurry or amendments to other tanks. This action is then repeated many times during the growth cycle in order to ensure the proper ratio of CO2 content (usually about 15%) to water at all times. The nutrients can be added at strategic times to promote more or less production without disrupting the algal growth cycles.

There is additional data that shows a subtle balance between growth cycle and lipid generation. It is understood that this system can be regulated to program cell starvation or cell colony generation through the use of computer or manual adjustment in the entrainment of amendments through the venturi in the static mixer, or other device.

Colony growth cycles are directly related to nutrient injection and light manipulation. Thus, this system is designed around the basic principles of flow manipulation and light enhancement. There are many species of aquatic organism that respond in different ways to growth stimuli. While examples micro-algae, diatoms and some prokaryotes show certain characteristics that are enhanced by light diffusion and micron mixing as described above, genetically modified feed stock of rapid growth and high lipid content can be use, which may require different parameters in regards to light and nutrients. This system is adaptable to those future stocks by variances in paddles sizes, injection ratios and other unforeseen modifications.

Figure 2:
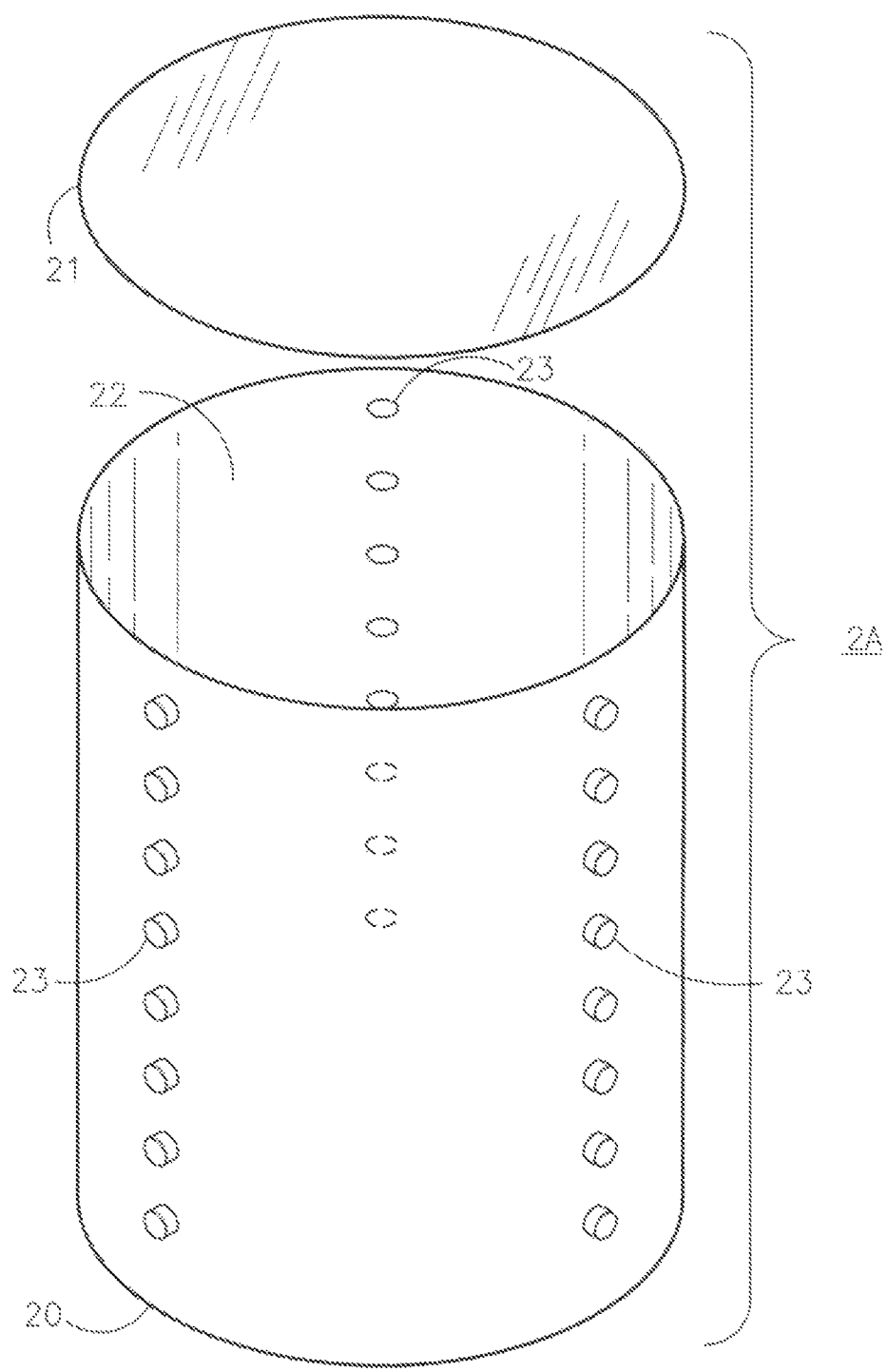
FIG. 2 shows a schematic diagram of a reaction chamber.

Reactor components are shown in greater detail in FIGS. 2-9. FIG. 2 shows an exemplary reaction vessel 20 with cover 21. In the walls of the vessel are mounted a number of light emitters or light sources 23. For example, such light emitters or light sources may be optical fibers or light emitting diodes (LEDs). In general, such LEDs or other light sources can be selected or modulated to provide a desired intensity. Likewise, the distribution of wavelengths can also be selected using particular selections of light sources and/or colored filters. The distribution of light sources can also be selected as desired, e.g., to maximize distribution of light throughout the reaction chamber. Instead of (or in addition to) light sources such as LEDs, optical fibers can be used to distribute light into the reaction chamber from the walls as well as from other locations. Light transmitted through optical fibers may be from any of a number of different sources, e.g., LEDs, natural light, concentrated natural light, and the like.

Figure 3:
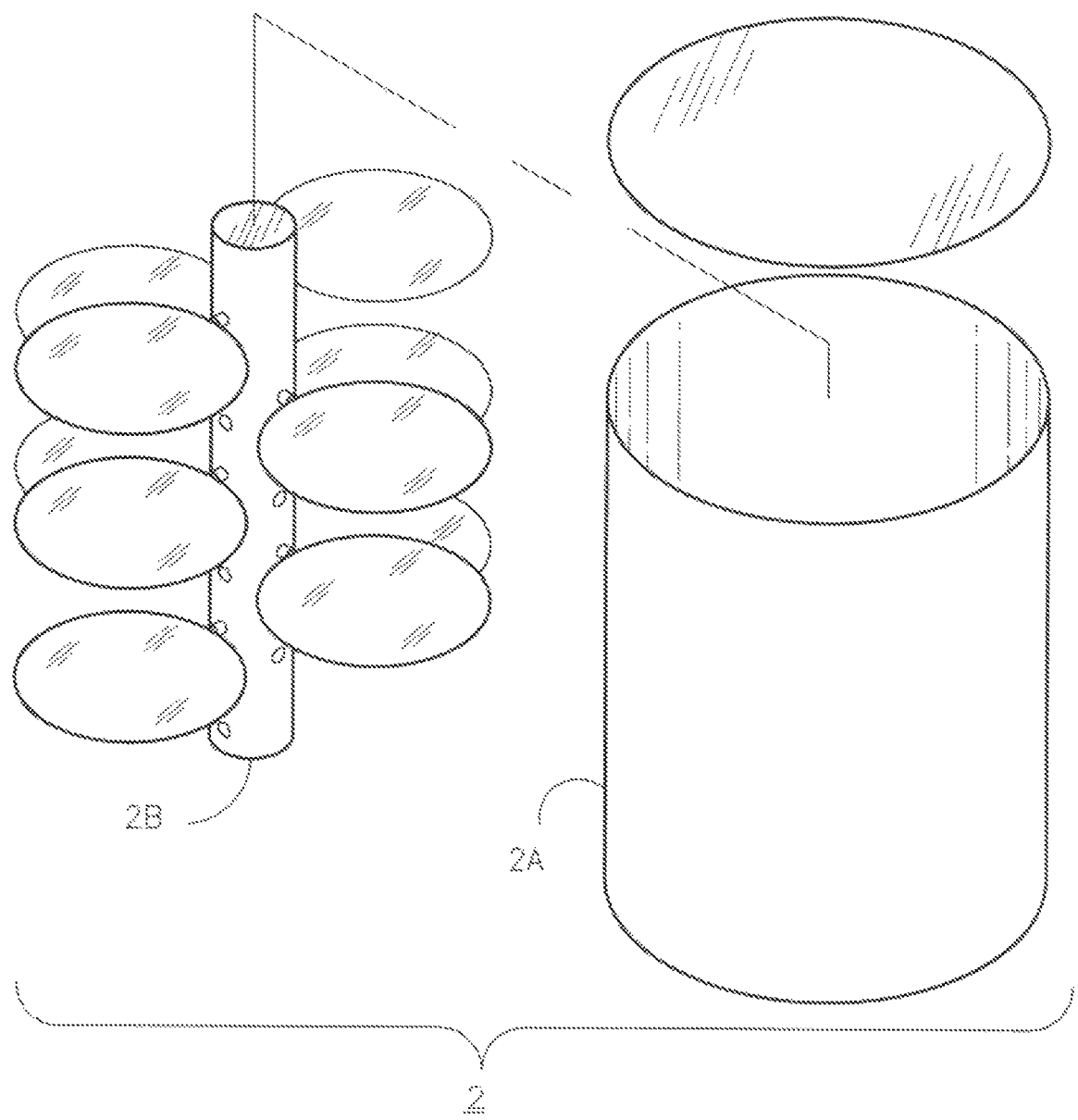
FIG. 3 shows a schematic representation of a reaction chamber and a dispensing rod that fits within the chamber.
Figure 4:
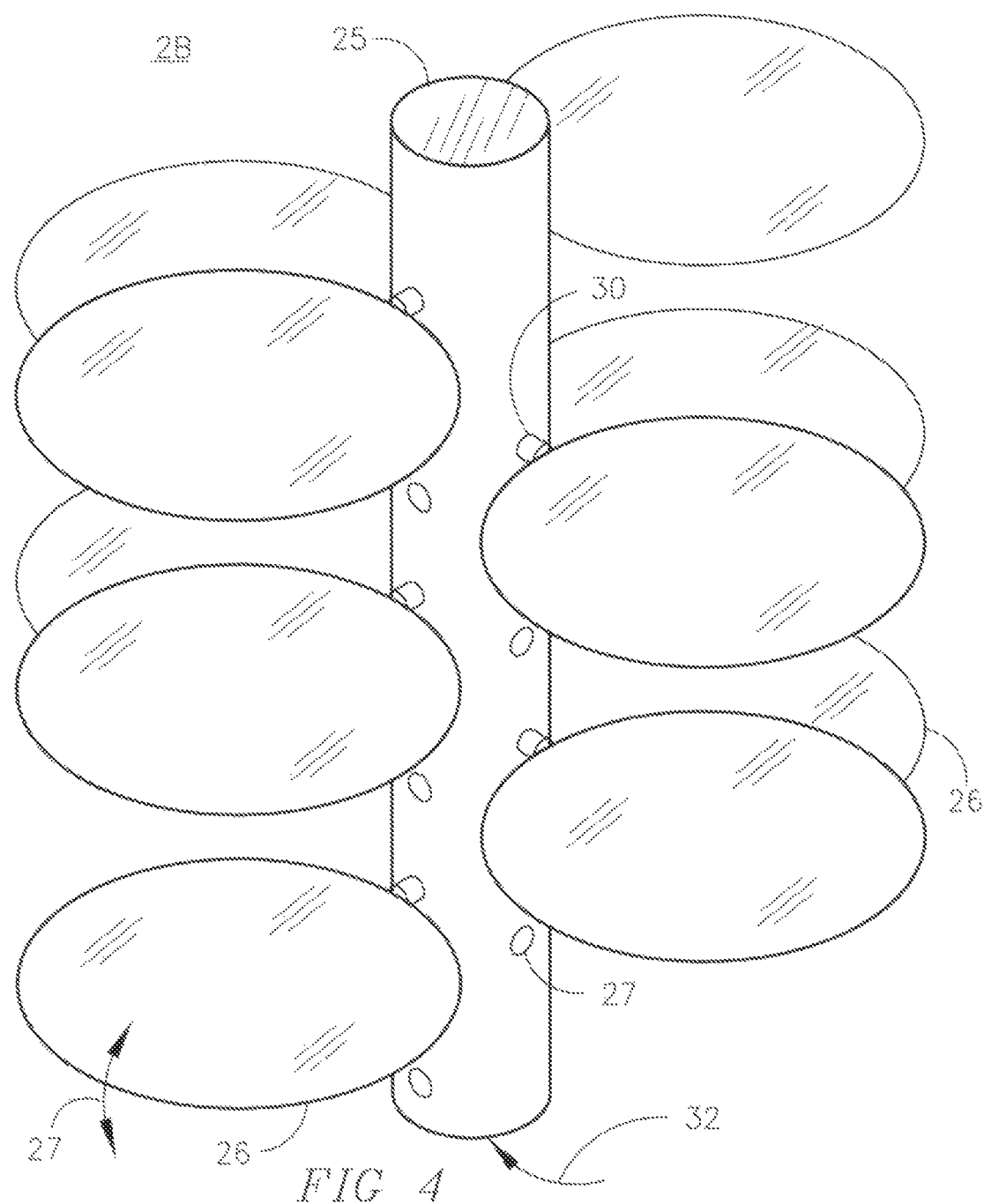
FIG. 4 shows a larger schematic view of a dispensing rod.

FIG. 3 shows both the tank portion 20 (identified as 2A) of the reactor as well as the flow dispensing rod (shown as component 2B). The designations 2A and 2B are used for the same purposes in FIGS. 2-6. The dispensing rod (2B) is shown in greater detail in FIG. 4, and is a multi-ported dispensing device having a central tube 25 to which is attached a plurality of area enhancing clear paddles 26 made of clear plastics or the like. The paddles are attached to the central tube through mounting studs or shafts 30. These paddles can, if desired, be tinted different colors to alter the wavelengths of light passing through the paddles, e.g., selected according to algal growth stock used to optimize growth rate. These paddles can also include UV retardants or accentuations, again depending on stock used.

The dispensing rod is usually centrally placed within a reaction chamber. The dispensing rod has a plurality of small holes or perforations 27 placed throughout the rod that disperse out either: the fine bubbles mix of CO2/nutrient for the incubated micro-algae stock, or micron/nano sized bubbles and /catalase enzymes as in the cell disruption cycles. End 32 of the dispensing rod can be used as the attachment end (e.g., using an attached flange) for forming a fluid connection with the mixing tank e.g., through a connection of the dispensing rod to the bottom of the reaction chamber. That is, in one configuration, a pipe leads from the mixing tank to the bottom of the reaction chamber and forms a sealed connection. Fluid passing through that pipe then passes through a that connection and through the bottom of the reaction chamber into the end 32 of the dispensing rod. The fluid then passes out through the apertures 23 and into the internal volume of the reaction chamber.

In a final cycle, ozone and/or alcohol micron mixed bubbles can be dispensed through the dispending rod for cleaning and disinfection. In this example, the tube is 1" in outer diameter and the outer vessel or bio-reactor diameter of 24". From the inner tube to the outer vessel's surface, the plurality of transparent paddles extend out to within about 2" of the walls of the reaction chamber, permitting a flow of water between the side walls and the edge of the paddles. The paddles are preferably in a wave form design though many other hydrodynamic forms can be used, such as helix, flat, curved, etc.

In this exemplary reactor, the paddles would therefore be roughly 9 inches long each. 9"+9"+1" (the tube)=20". The paddles are mounted on thin axles or shafts running through the 1" tube. The axles can permit limited rotation or can be fixed to both the tube and the paddles so that there is no rotation of the paddles. The paddles typically accomplish 3 things:

1. Increased surface area for light distribution. As indicated above, the paddles can be tinted different colors, such as red, blue or green to create different lighting environs to promote micro-algae growth.

2. Creation of eddies to promote increased growth of micro-algae. In has been found that areas of ocean eddies can be regions of high microorganism growth. The same effect can be advantageously used in the present growth vessels.

3. Motion inhibition. The plurality of paddles, while forcing fluids to the outer part of the paddle has the effect of creating a Bernoulli Effect. The placement of the paddles accomplishes two things: 1 a reduction in fluid velocity throughout the vessel, the creation of high pressure zones on the exterior of the part of the inner vessel which then accentuate the creation of eddies on the back side of the paddles These eddies are correspondingly slower in overall fluid velocities thereby creating growth zones. The placement of these paddles will dictate the overall flow rate within the reaction vessel. It is anticipated that the paddles could be positioned on a staggered basis, or any other configuration to decrease flow rate while accentuating high and low pressure zones. The slower overall fluid velocities are believed to be advantageous in view of reports indicating reduced growth in high shear environments. In one such study, the effect of shear flow on the green alga Scenedesmus quadricauda grown in Bristol's medium was tested. The shear flow was generated using a Couette type rotating cylinder apparatus. Growth of Scenedesmus quadricauda, measured in terms of chlorophyll A concentration, was inhibited under different fluid motions. Inhibition was most pronounced at high Reynolds number (Re) and the corresponding mean rate of energy dissipation ($\epsilon$). Algal growth was maximum during the stagnant fluid flow experiment. The flocs comprised of dead and living cells of algae formed as a result of shear flow. Cell morphometry did not change consistently under different flow conditions but cell destruction was evident.

Figure 5:
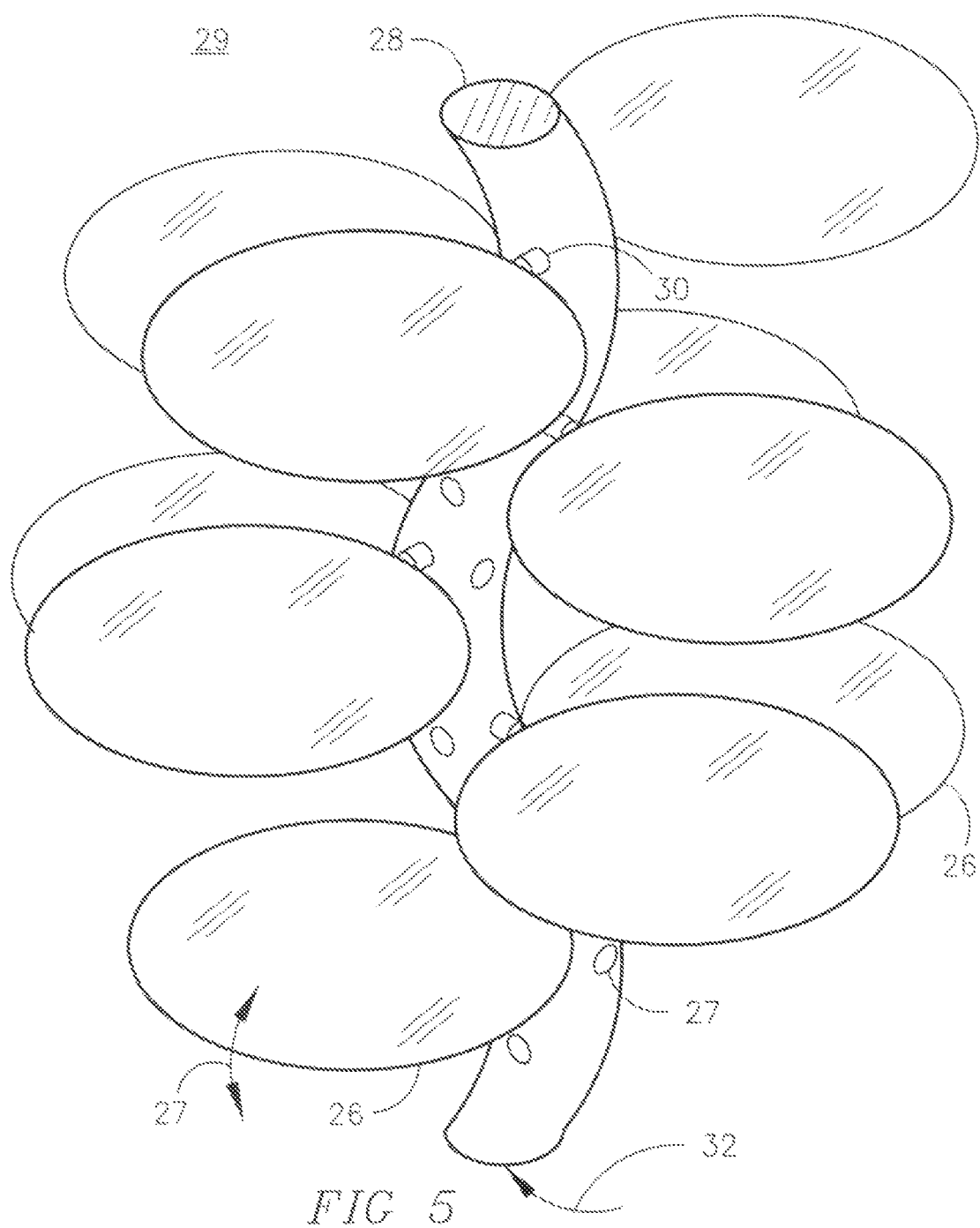
FIG. 5 shows a schematic view of a dispensing rod with a wavy central tube.

An alternate tube shape in a dispensing rod is illustrated in FIG. 5, where the central tube 28 is a wavy shape.

Figure 6:
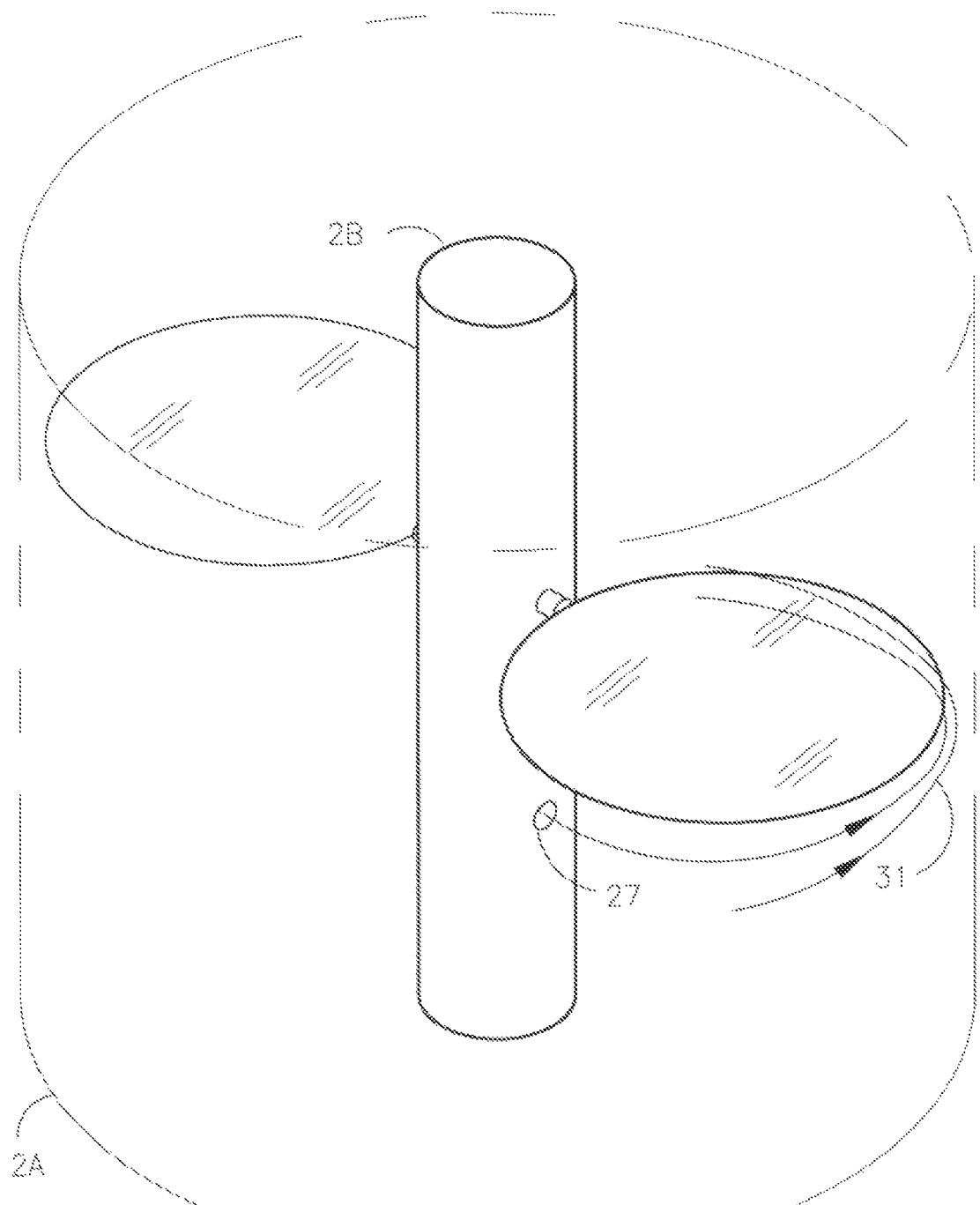
FIG. 6 shows s simplified schematic view of a dispensing rod installed in a reaction chamber, with the flow of medium out of the central tube and around paddles of the dispensing rod.

FIG. 6 shows a simplified dispensing rod mounted in the reactor tank. The arrows 31 illustrate the flow of medium out of the dispensing hole 27 and flowing around the paddle, enhancing eddy formation while also limiting flow.

Figure 7:
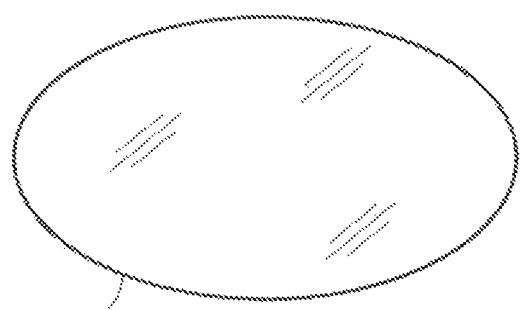
FIGS. 7, 8, and 9 show paddles for use on a dispensing rod and having examples of alternate shapes.
Figure 8:
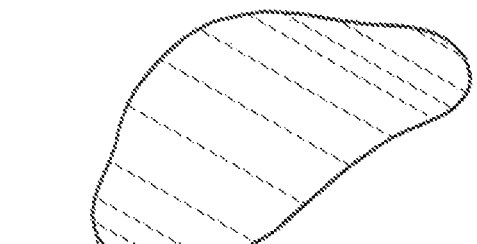
Figure 9:
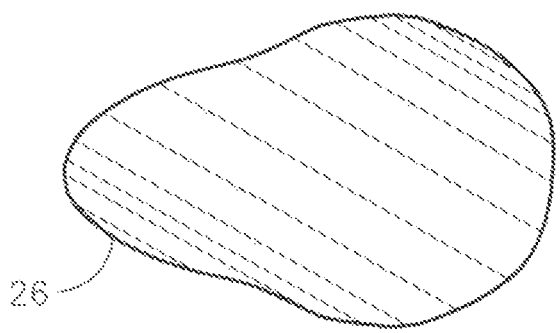

Alternate paddle shapes are shown in FIGS. 7, 8, and 9. The paddle shape or shapes can be selected (e.g., empirically) to provide desired culture properties, such as eddy characteristics, light emission area, flow inhibition, and the like.

Of course, the reactor, as well as other components of the system, can be constructed in many different ways. The system and components shown are only illustrative.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to the organism being grown, the growth conditions, and the configuration of the system. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values or value range endpoints are provided for embodiments, additional embodiments are described by taking any 2 different values as the endpoints of a range or by taking two different range endpoints from specified ranges as the endpoints of an additional range. Such ranges are also within the scope of the described invention. Further, specification of a numerical range including values greater than one includes specific description of each integer value within that range.

Thus, additional embodiments are within the scope of the invention and within the following claims.

What is claimed is:

1. A system for culturing photosynthesizing microorganisms, comprising:
   a source of a gaseous fluid comprising a nutrient for growing photosynthetic miocroorganisms;
   a mixer which creates micron bubbles within an aqueous medium using the gaseous fluid;
   a mixing chamber in fluid communication with said mixer, the mixing chamber holding the micron bubbles and aqueous medium and attenuating a shock wave generated from the creation of the micron bubbles;
   a reaction chamber holding a culture of photosynthesizing microorganisms, the reaction chamber in fluid communication with said mixing chamber and comprising a fluid dispensing rod that introduces the aqueous medium into the culture of photosynthesizing microorganisms, thereby dispersing the nutrient in the culture of photosynthesizing microorganisms; and
   wherein said fluid dispensing rod comprises a tube comprising at least one internal fluid path, a plurality of light conducting panels attached around said tube, and at least one light path that provides for light emission from the light conducting panels.

2. The system of claim 1, wherein said mixer comprises a static mixer.

3. The system of claim 2, wherein said static mixer comprises a flow constrictor and an entrainment tube immediately upstream thereof, wherein said entrainment tube delivers a gas or a liquid or both into a fluid stream passing through said mixer.

4. The system of claim 1, wherein the tube of said fluid dispensing rod comprises a plurality of perforations.

5. The system of claim 1, wherein said reaction chamber comprises an inwardly directed minored surface.

6. The system of claim 1, wherein said at least one light path is oriented to direct the light emission from the light conducting panels into said reaction chamber.

7. The system of claim 6, wherein the light conducting panels comprises a plurality of light emitting diodes (LEDs).

8. The system of claim 7, wherein the light conducting panels are configured to mix the aqueous medium in the reaction chamber.

9. The system of claim 1, further comprising a collection tank having fluid connection with said reaction chamber.

10. The system as in claim 1, wherein the micron bubbles have an average diameter of less than 100 microns.

11. The system as in claim 1, wherein the micron bubbles have an average diameter of less than 70 microns.

12. The system as in claim 1, wherein the micron bubbles have an average diameter of less than 40 microns.

13. The system as in claim 1, wherein the nutrient comprises carbon dioxide.

14. The system as in claim 1, wherein the dispensing rod is movable within the reaction chamber thereby dispersing the aqueous medium.

15. A system for culturing photosynthesizing microorganisms, comprising:
- a source of a gaseous fluid comprising a nutrient for growing photosynthetic microorganisms;
- a mixer which creates micron bubbles within an aqueous medium using the gaseous fluid;
- a mixing chamber in fluid communication with said mixer, the mixing chamber holding the micron bubbles and aqueous medium and attenuating a shock wave generated from the creation of the micron bubbles;
- a reaction chamber holding a culture of photosynthesizing microorganisms, the reaction chamber in fluid communication with said mixing chamber and comprising a light distributing and fluid dispensing rod that introduces the aqueous medium into the culture of photosynthesizing microorganisms, thereby dispersing the nutrient in the culture of photosynthesizing microorganisms; and
- wherein said light distributing and fluid dispensing rod comprises a tube comprising at least one internal fluid path, a plurality of light conducting panels attached around said tube, and at least one light path that provides for light emission from the light conducting panels.

16. The system of claim 15, wherein said reaction chamber comprises an inwardly directed mirrored surface.

17. A system, comprising:
- a source of a gaseous fluid;
- a mixer which creates micron bubbles within an aqueous medium using the gaseous fluid;
- a mixing chamber in fluid communication with said mixer, the mixing chamber holding the micron bubbles and aqueous medium and configured to attenuate a shock wave generated from the creation of the micron bubbles;
- a reaction chamber in fluid communication with said mixing chamber, the reaction chamber comprising a fluid dispensing rod that introduces the aqueous medium into a culture of photosynthesizing microorganisms following attenuation of the shock wave within the mixing the chamber;
- a collection tank in fluid communication with said reaction chamber; and
- wherein said fluid dispensing rod comprises a tube comprising at least one internal fluid path, a plurality of light conducting panels attached around said tube, and at least one light path that provides for light emission from the light conducting panels.

18. The system of claim 17, wherein said reaction chamber comprises an inwardly directed mirrored surface.

* * * * *